(12) United States Patent
Mattson et al.

(10) Patent No.: US 7,822,173 B2
(45) Date of Patent: Oct. 26, 2010

(54) SMART RADIATION DETECTOR MODULE

(75) Inventors: Rodney A. Mattson, Mentor, OH (US);
Marc A. Chappo, Elyria, OH (US);
Randall P. Luhta, Highland Heights, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 70 days.

(21) Appl. No.: 12/159,861

(22) PCT Filed: Jan. 4, 2007

(86) PCT No.: PCT/US2007/060083

§ 371 (c)(1),
(2), (4) Date: Jul. 2, 2008

(87) PCT Pub. No.: WO2007/082128

PCT Pub. Date: Jul. 19, 2007

(65) Prior Publication Data

US 2008/0298541 A1    Dec. 4, 2008

Related U.S. Application Data

(60) Provisional application No. 60/766,385, filed on Jan. 16, 2006.

(51) Int. Cl.
*G01N 23/00*    (2006.01)

(52) U.S. Cl. .............................. 378/19; 378/4
(58) Field of Classification Search ............... 378/4–20
See application file for complete search history.

(56) References Cited

U.S. PATENT DOCUMENTS

| | | | |
|---|---|---|---|
| 5,532,484 A * | 7/1996 | Sweetser et al. | 250/332 |
| 6,426,991 B1 | 7/2002 | Mattson et al. | |
| 6,453,008 B1 | 9/2002 | Sakaguchi et al. | |
| 6,510,195 B1 | 1/2003 | Chappo et al. | |
| 6,667,482 B2 | 12/2003 | Von Der Haar | |
| 6,879,660 B2 | 4/2005 | Dhawale et al. | |
| 6,932,507 B2 | 8/2005 | Winkelmann | |
| 7,136,454 B2 * | 11/2006 | Gerndt et al. | 378/98.12 |
| 2002/0148968 A1 | 10/2002 | Von Der Haar | |
| 2004/0022352 A1 * | 2/2004 | Suzuki | 378/19 |
| 2005/0017187 A1 | 1/2005 | Petrick et al. | |
| 2005/0063513 A1 | 3/2005 | Hsieh et al. | |
| 2005/0123090 A1 | 6/2005 | Heismann et al. | |
| 2005/0133745 A1 | 6/2005 | Haug et al. | |

* cited by examiner

*Primary Examiner*—Hoon Song

(57) ABSTRACT

An ionizing radiation detector module (22) includes a detector array (200), a memory (202), signal processing electronics (208), a communications interface (210), and a connector (212). The memory contains detector performance parameters (204) and detector correction algorithms (206). The signal processing electronics (208) uses the detector performance parameters (204) to correct signals from the detector array (200) in accordance with the detector correction algorithms (206).

17 Claims, 3 Drawing Sheets

SMART RADIATION DETECTOR MODULE

CROSS REFERENCE TO RELATED APPLICATIONS

This application claims the benefit of U.S. provisional application Ser. No. 60/766,385 filed Jan. 16, 2006, which is incorporated herein by reference.

The present invention finds particular application to radiation detectors used in computed tomography (CT) scanners. It also finds application to other radiation sensitive detectors, and especially in situations where it is desirable to correct for variations in detector performance.

CT scanners have proven to be invaluable in providing information indicative of the internal structure of an object. In medical imaging, for example, CT scanners are widely used to provide images and other information about the physiology of human patients. Recent years have seen the rapid adoption of multi-slice CT, as increasing the number of slices or channels can have a number of advantages, such as an improved ability to scan the heart and other moving portions of the anatomy, shorter scan times, improved scanner throughput, improved axial resolution and coverage, and the like.

One consequence of this trend, however, is that CT detector modules are becoming increasingly complex and expensive. Indeed, the detector is often one of the most expensive components, if not the most expensive component, of a CT scanner.

By way of one example, state of the art CT scanners are designed to provide as many as 128 slices in one revolution. In such a system, a typical detector module may contain as may as 2048 (16×128) individual detector pixels. The detector would typically contain a number of modules, so that an exemplary detector may contain as many as 80,000 individual detector pixels. In turn, each detector pixel typically includes a scintillator, a photodiode, mechanical supports, optical and electrical interfaces, and associated electronic signal conditioning circuitry. Each of these items can influence the performance characteristics of the detector pixel and the detector module as a whole.

As the number of detector pixels increases, it becomes increasingly likely that variations in detector performance will become significant. For example, individual detector pixels may have differing performance characteristics or may even be entirely inoperative. Moreover, even for a nominally identical detector design, detector performance characteristics may vary from vendor to vendor, or even lot to lot.

It is desirable to reduce the impact of these variations. For example, manufacturing yields can be improved, and costs reduced, if performance variations can be identified and corrected, rather than discarding or reworking a detector module. Viewed from one perspective, detector yield can be improved by allowing for relatively wider performance limits. Viewed from another perspective, identifying and correcting for performance variations will, for a given set of detector acceptance criteria, generally provide improved detector performance. Servicing of detectors modules can also be simplified by reducing the situations in which it is necessary to replace a detector module. Where it is necessary to replace a detector module, it is desirable to reduce the need for additional detector or scanner calibrations.

Some corrections may be made by the reconstruction computer as part of the image reconstruction process. As will be appreciated, however, another trend has been a demand for ever shorter reconstruction times, together with a requirement to reconstruct ever increasing amounts of data and numbers of image slices. Unfortunately, the task of identifying and applying the necessary corrections during reconstruction tends to increase overall system complexity and can also have a deleterious impact on reconstructor performance.

Aspects of the present invention address these matters, and others.

According to a first aspect of the invention, a computed tomography apparatus includes an x-ray source, a plurality of x-radiation sensitive detector modules and a reconstructor which generates volume space data indicative of x-radiation detected by the detector modules. The detector modules include an x-radiation sensitive detector array which generates electrical signals in response to x-radiation detected thereby, a memory which contains a first parameter indicative of a measured performance characteristic of the detector module, and circuitry in operative communication with the memory which corrects the electrical signals as a function of the first parameter so as to generate corrected detector signals.

According to another aspect of the invention, an x-ray detector module is adapted for use in an imaging apparatus which utilizes a plurality of detector modules disposed so as to form a tiled two dimensional array of detector pixels. The detector module includes a plurality of x-ray sensitive detector pixels which generate signals in response to detected x-rays. The pixels are arranged for installation in the tiled two-dimensional array. The detector module also includes a memory which contains data indicative of the performance of the detector pixels, signal correction circuitry in operative communication with the memory and the detector pixels, and an electrical connector for selectively electrically connecting the detector module to the imaging apparatus. The signal correction circuitry corrects the detector pixel signals as a function of the data so as to generate corrected signals.

According to another aspect of the invention, an imaging apparatus includes an ionizing radiation source, a radiation detector which detects radiation emitted by the radiation source, and a reconstructor which generates volumetric data indicative of the radiation detected by the radiation detector. The radiation detector includes a plurality of detector modules, each of which includes means for generating electrical signals indicative of detected radiation, means for storing data indicative of the performance of the detector modules, means for using the data to correct the electrical signals, and means for selectively connecting the detector module to the detector.

Those skilled in the art will appreciate still other aspects of the present invention upon reading and understanding the attached figures and description.

The present invention is illustrated by way of example and not limitation in the figures of the accompanying drawings, in which like references indicate similar elements and in which.

Figure 1:
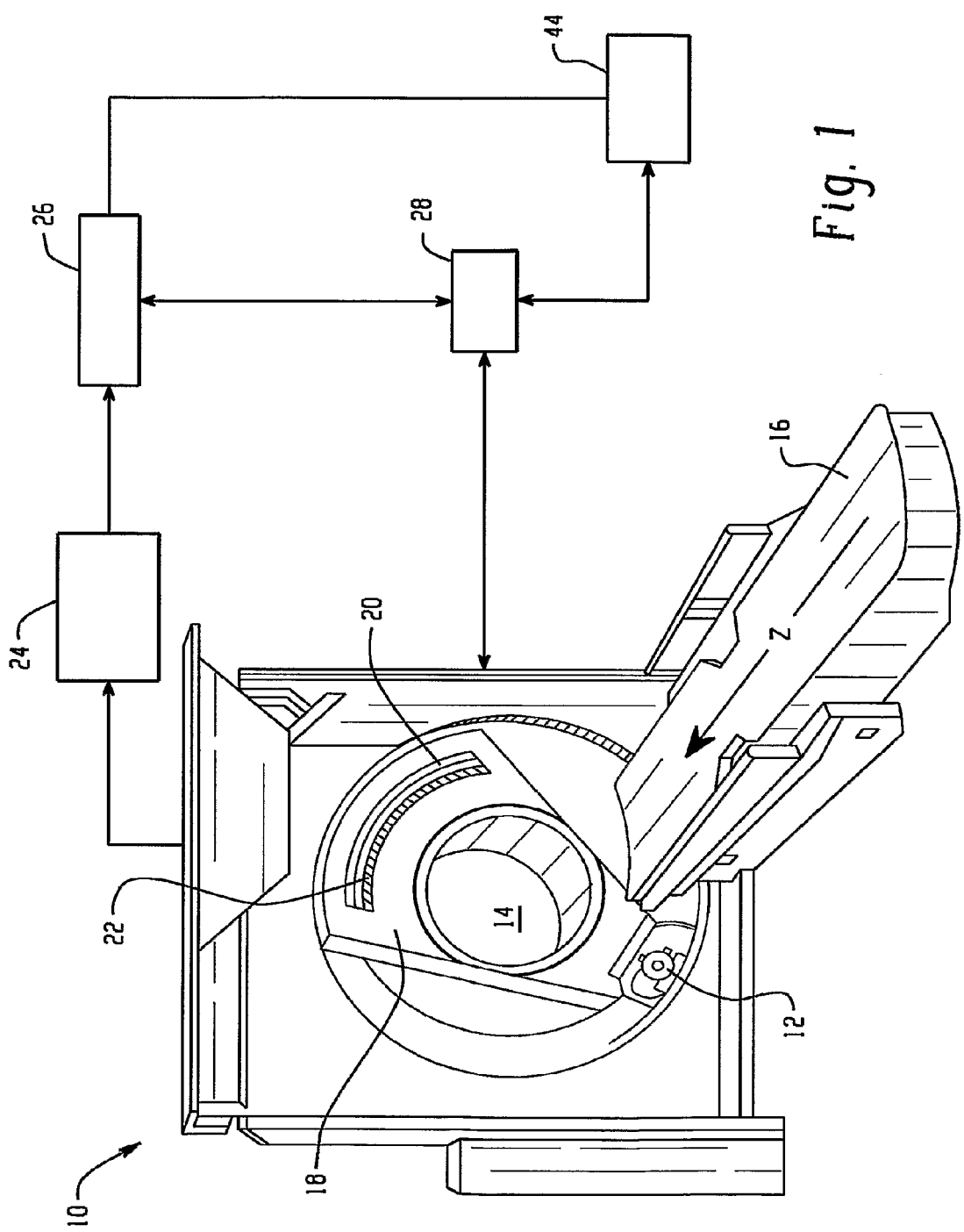
FIG. 1 depicts a CT scanner.

With reference to FIG. 1, a CT scanner 10 includes a rotating gantry portion 18 which rotates about an examination region 14. The gantry 18 supports a radiation source 12 such as an x-ray tube. The gantry 18 also supports an x-ray sensitive detector 20 which subtends an arc on the opposite side of the examination region 14. X-rays produced by the x-ray source 12 traverse the examination region 14 and are detected by the detector 20. An object support 16 supports an object such as human patient in the examination region 14. The support 16 is preferably movable in coordination with the rotation of the gantry 18 so as to provide helical scanning.

The detector 20 includes an arcuate array of detector modules 22 arranged so as to form a two dimensional array of detector pixels. The detector modules are preferably arranged in a tiled array in which the pixels in an array abut the pixels in adjacent arrays. In one implementation, the detector 20 includes one hundred twenty eight (128) or more slices. Suitable detector implementations are further described in commonly assigned U.S. Pat. No. 6,510,195, entitled Solid State X-Radiation Detector Module and Mosaics Thereof, and an Imaging Method and Apparatus Employing the Same, which is expressly incorporated by reference herein in its entirety, although other detector implementations are also possible. Note also that the arrays may be irregular. For example, pixels in one or more rows or columns may be offset from one another.

A so-called fourth generation scanner configuration, in which the detector 20 spans an arc of 360 degrees and remains stationary while the x-ray source 12 rotates, as well as flat panel detectors, may also be implemented. Detector having greater or lesser number of slices may likewise be implemented.

As will be further discussed below, readout electronics associated with each detector module 22 receive signals originating from the various detector pixels and provide signal conditioning, analog to digital conversion, multiplexing, and like functionality. Certain detector specific performance information is also stored in memory associated with detector module 22 and is preferably used to provide a corrected detector output signal.

A data acquisition system 24 preferably carried by the rotating gantry 18 receives output signals from a plurality of detector modules 22 and provides additional multiplexing, data communication, and like functionality. A reconstructor 26 reconstructs the data obtained by the detector 20 to form volumetric image data indicative of the object under examination.

A general purpose computer serves an operator console 44. The console 44 includes a human-readable output device such as a monitor or display and an input device such as a keyboard and mouse. Software resident on the console allows the operator to control the operation of the scanner by establishing desired scan protocols, initiating and terminating scans, viewing and otherwise manipulating the volumetric image data, and otherwise interacting with the scanner.

A controller 28 coordinates the various scan parameters as necessary to carry out a desired scan protocol, including x-ray source 12 parameters, movement of the patient couch 16, and operation of the data acquisition system 26.

Figure 2:
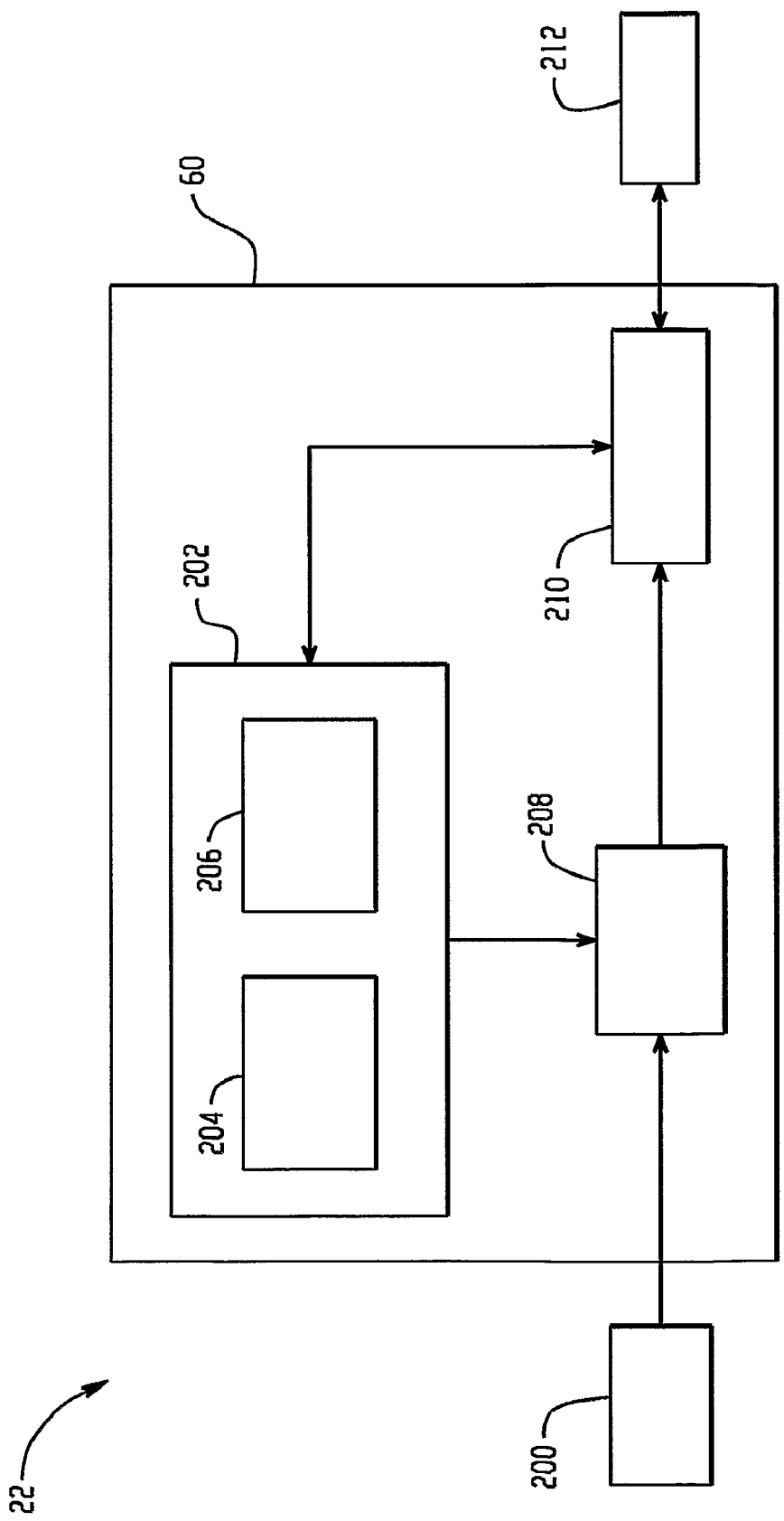
FIG. 2 is a functional block diagram of a detector module for a CT scanner.

FIG. 2 is a functional block diagram of a detector module 22. The detector module 22 includes one more detector arrays 200, readout electronics 60, and one or more connectors 212. The detector array(s) 200, readout electronics 60, and connector are mounted to or carried by a suitable printed circuit board or other substrate for assembly in the detector 20. The detector module 22 may also include multiple substrates.

The detector array 200 includes an n×m array of detector pixels, with each detector pixel including a scintillator in optical communication with a photodiode. Back contact or back illuminated photodiodes facilitate the fabrication of relatively larger arrays, although front illuminated or other photodiode structures may also be used. Other detector array 200 implementations, such as multiple energy, solid state, or direct conversion detectors, are also contemplated. In one embodiment, each detector array 200 includes a 16×16 array of detector pixels, and the detector module 22 includes eight (8) detector arrays 200 arranged so as to form a 16×128 array.

The readout electronics 60, which receives and processes signals generated by the various detector pixels, can be implemented as a microprocessor based application specific integrated circuit (ASIC) which includes an operatively connected memory 202, signal processing electronics 208, and communications interface 210.

The signal processing electronics 208 includes multiplexing, amplification and filtering, analog to digital conversion, signal correction, and like circuitry for processing the signals generated by the various detector pixels.

The memory 202 includes detector performance parameters 204 and detector correction algorithms 206. Exemplary detector performance parameters 204 include one or more of detector afterglow, cross talk, linearity, pixel operative/inoperative status, gain, offset, and silicon hole trapping data, although information relating to additional or different performance characteristics may also be stored. Depending on the particular performance characteristic and the characteristics of a particular detector, the relevant parameters are stored individually for each detector pixel. One or more of the parameters may also be stored for use in connection with the detector array 200 or the detector module 22 as a whole, especially where the performance characteristic is expected to be relatively uniform for the various detector pixels in the detector array 200 or the detector module 22 as a whole.

The correction algorithms 206 are stored as computer readable instructions which, when carried out by the microprocessor, use the relevant detector performance parameters 204 to carry out the desired corrections. In this regard, it should be noted that it is not necessary that the parameters 204 and algorithms 206 be stored in the same physical memory. Exemplary detector correction algorithms include corrections for detector afterglow, cross talk, linearity, inoperative detector elements, gain, offset, and silicon hole trapping corrections, although additional or different corrections may be applied. A temperature correction may also be applied at the detector level. Some or all of the corrections are preferably applied in real time during operation of the scanner 10 so that corrected detector signals are supplied to the reconstructor 26.

Also associated with each detector module 22 is a serial number or similar identifier. Additional information, such as date codes, manufacturer or vendor information, or the like may also be associated with the detector module 22. The information may be stored in the memory 202. Some or all of the information may also be provided on a bar code or other computer readable designator, human readable designator, traveler, or the like associated with the detector module 22 or its individual components. Such an arrangement is particularly advantageous where some or all of the components of a detector module 22 are characterized prior to assembly in the detector module 22. In such a situation, the performance characteristics associated with a particular component may be stored in a database and the performance parameters 204 loaded into the memory 202 of the appropriate detector module 22 in a subsequent manufacturing step.

The communication interface 210 provides communications between the data acquisition circuitry 24, the memory 202, and the signal processing electronics 208. One or more electrical connectors 212 allow the detector module 22 to be electrically connected to the detector 20 during the manufacturing process. The connector(s) 212 preferably also facilitate field replacement of the detector nodule 22, if needed.

It should also be noted that the readout electronics 60 do not necessarily include a microprocessor. In such an implementation, the various corrections may be implemented using one more digital signal processors (DSPs), field programmable gate arrays (FPGAs), or other suitable digital or analog electronic circuitry. The readout electronics 60 may also be implemented using multiple ASICs, integrated circuits, discrete components, or a combination thereof.

In addition, one or more detector modules 22 may be combined to form a still larger detector module. In such an implementation, some or all of the readout electronics 60 may be apportioned between the detector modules 22 and the larger module.

Figure 3:
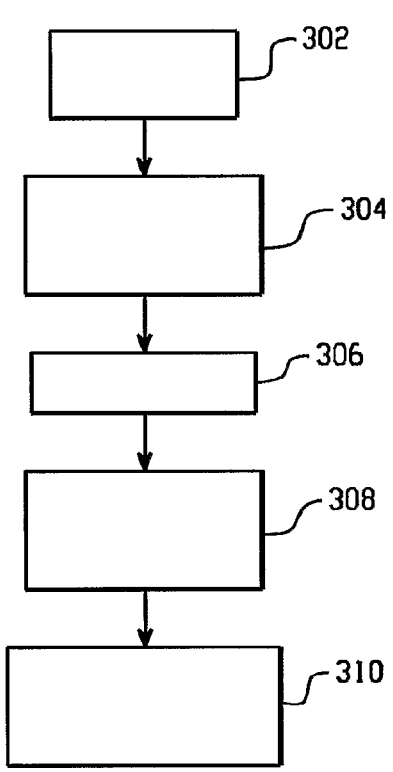
FIG. 3 depicts a process for characterizing a detector module.

An exemplary process for characterizing a detector module 22 during manufacturing is depicted in FIG. 3. At 302, a unique identifier is assigned to the detector module. Where detector components are characterized individually, unique identifiers are also assigned to the individual components.

The detector performance is characterized at step 304. As noted above, the characterization may be performed at different assembly levels. For example, it may be desirable to characterize certain of the parameters at the component level, others at the module level, or still others at the detector 20 or scanner 10 levels.

One exemplary characterization is a test for crosstalk between detector pixels, which is more readily performed at the detector module level. Another is a test for inoperative pixels, in which inoperative pixels are identified. Such a test is again more readily performed at the detector module level. Detector modules 22 having several inoperative pixels in proximity to each other, or inoperative edge pixels for which sufficient neighboring pixel data is unavailable, are rejected. Otherwise, the locations of the inoperative pixels are identified.

Detector offset, on the other hand, is often evaluated at the beginning of an actual scan. Other performance tests, such as those for detector gain, afterglow, linearity, and the like are well known to those skilled in the art and may also be readily implemented at the desired level.

The test results are stored at step 306, for example in a test database, in a traveler which accompanies the particular component, or the like. In this regard, it should be noted that the temporal sequence in which the individual components or modules are tested is not critical. Of course, testing performed at a given assembly level should be performed after the various components have been assembled to form the desired assembly level.

At step 308, the detector performance parameters 204 are loaded into the memory 202 of a given detector module. Where one or more components were characterized at the component level, the characteristics of the particular component are obtained from the database. In one implementation, the performance parameters 204 are communicated to the detector module 22 via the communications interface 210. Note that the communication of the relevant parameters may be performed at a convenient level in the assembly process, for example before or after the detector module 22 has been installed in the detector 20 or the scanner 10. Moreover, some or all of the parameters 204 may be stored in the memory 202 before it is installed in the particular detector module 22. It may also be desirable to load different correction algorithms 206 into the memory 202 depending on the characteristics of a particular detector module 22.

Final detector 20 and scanner 10 characterization and testing is performed as needed at step 310.

Figure 4:
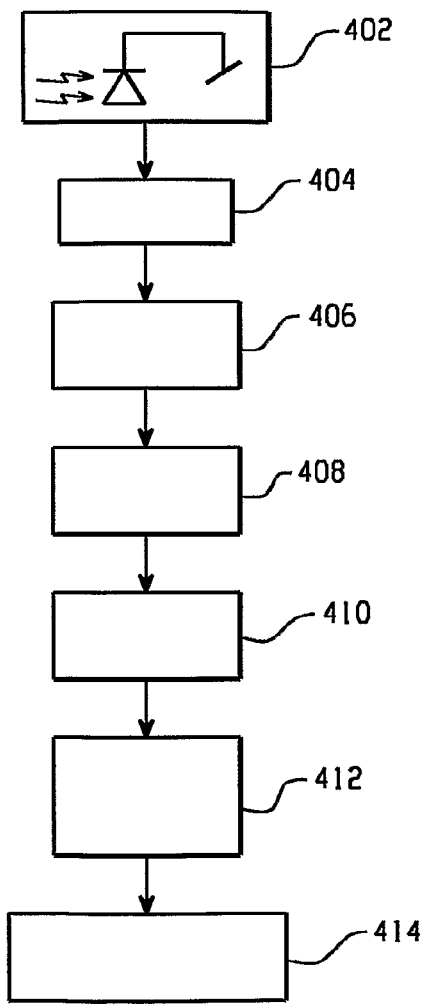
FIG. 4 depicts an exemplary detector correction process.

As noted above, the demands on the reconstructor 26 can be reduced if some or all of the corrections are performed on the detector signals in or near real time before they are presented to the reconstructor 26. An exemplary correction process is depicted in FIG. 4. While FIG. 4 describes the process for a single detector pixel, it will of course be understood that the other detector pixels are similarly corrected.

At 402, a given detector pixel generates a signal indicative of the radiation detected during a scan. The signal converted to digital form at step 404.

A detector offset correction is performed at step 406. As noted above, detector offset is typically measured at the beginning of every scan in the absence of x-rays from the source, with the offset information stored in the memory 202.

A gain correction is performed at step 408 using data from the memory 202. Similarly, a cross talk correction is performed at step 410. In one implementation, the signals generated by detector pixels or modules having a relatively high cross talk are corrected to reduce cross talk effects. In another implementation, cross talk is added to detector pixels or modules exhibiting a relatively low cross talk. An inoperative pixel correction is applied at step 412. For pixels identified as defective, temporally corresponding signals from one or more neighboring detector pixels are interpolated in or near real time to produce a signal which approximates that of the inoperative pixel. This signal is used to replace the signal from the otherwise inoperative pixel. Of course, still additional, different, subsets of the above corrections may also be applied.

In any case, the corrections are applied in or near real time during scanning so that corrected signals are supplied to the reconstructor 26.

Still other corrections may be performed upstream. For example, a global or system gain correction, which is typically based on a scanner air calibration, is applied by the reconstructor 26 at 414.

It is also not necessary to perform all of the necessary corrections at the detector module level. Thus, some or all of the detector performance parameters 202, for example those relating to detector linearity and afterglow, may be uploaded to the scanner 10 via the communication interface 210 as part of the scanner calibration process, with the corrections performed by the reconstructor 26 or other upstream. Alternatively, the module identifier may be uploaded and the corresponding parameters obtained from a database.

The performance characteristics of a particular detector pixel or detector module 22 may also change during the life of the scanner. As just one example, a previously functional detector pixel may become inoperative. Once the inoperative pixel has been identified, typically during servicing of the scanner, the location of the pixel is communicated to the relevant memory 202 via the communication interface 210. The locations of other inoperative pixels may also be identified by querying the detector module 22. Alternately, the signal processing electronics 208 may be configured to automatically detect inoperative pixels during calibration or otherwise during operation of the scanner. If the number or location of inoperative pixels meets a desired acceptance criteria, the output of the particular pixel is synthesized as described above during operation of the scanner. If the acceptance criteria are not satisfied, the detector module 22 is preferably repaired or replaced. A similar procedure may be applied to account for changes in other detector parameters.

Of course, modifications and alterations will occur to others upon reading and understanding the preceding description. It is intended that the invention be construed as including all such modifications and alterations insofar as they come within the scope of the appended claims or the equivalents thereof.

What is claimed is:

1. In a computed tomography apparatus including an x-ray source, a plurality of x-radiation sensitive detector modules and a reconstructor which generates volume space data indicative of x-radiation detected by the detector modules, the detector modules comprising:
- an x-radiation sensitive detector array which generates electrical signals in response to x-radiation detected thereby;
- a memory which contains both a first parameter indicative of a first measured performance characteristic of the detector module and a second parameter indicative of a second measured characteristic of the detector module;
- circuitry in operative communication with the memory which corrects the electrical signals as a function of the first parameter so as to generate corrected detector signals; and
- a communication interface, in operative communication with the memory, configured to communicate the second parameter to a device external to the detector module, wherein the device is configured to correct the corrected detector signals as a function of the second parameter.

2. The apparatus of claim 1 wherein the detector array includes a plurality of detector pixels and wherein the first parameter includes a parameter indicative of a measured performance characteristic of individual pixels in the array.

3. The apparatus of claim 2 wherein the parameter identifies inoperative pixels.

4. The apparatus of claim 3 wherein the circuitry uses a temporally corresponding signal from a pixel in the neighborhood of an inoperative pixel to correct for the inoperative pixel.

5. The apparatus of claim 2 wherein the measured performance characteristic is crosstalk between pixels in the array.

6. The apparatus of claim 1 wherein the first performance characteristic is measured prior to installation of the detector module in the computed tomography apparatus.

7. The apparatus of claim 6 wherein the detector module includes a component, wherein the first parameter is indicative of a measured performance characteristic of the component, and wherein the performance characteristic of the component is measured prior to installation of the component in the detector module.

8. The apparatus of claim 1 wherein the detector module includes a communication interface in operative communication with the memory and adapted to receive data indicative of a measured performance characteristic from a source external to the detector module.

9. The apparatus of claim 1 wherein the detector module includes a computer readable storage medium containing instructions which, when executed by a computer processor, cause the computer processor to carry out a method which includes using the first parameter to correct the electrical signals.

10. An x-ray detector module for use in an imaging apparatus, the detector module comprising:
- a plurality of x-ray sensitive detector pixels which generate signals in response to detected x-rays;
- a memory which contains first and second data indicative of the performance of the detector pixels;
- signal correction circuitry in operative communication with the memory and the detector pixels, wherein the signal correction circuitry corrects the detector pixel signals as a function of the first data so as to generate corrected signals;
- a communication interface, in operative communication with the memory, configured to communicate the second parameter to a device external to the detector module, wherein the device is configured to correct the corrected detector signals as a function of the second parameter.

11. The detector module of claim 10 wherein the first data includes data indicative of a first performance characteristic which is determined prior to installation of the detector module in the imaging apparatus.

12. The detector module of claim 11 wherein the second data includes data indicative of a second performance characteristic which is determined subsequent to installation of the detector module in the imaging apparatus.

13. The detector module of claim 12 wherein the second performance characteristic is detector offset.

14. The detector module of claim 11 wherein the first data includes data indicative of a plurality of performance characteristics which are determined prior to installation of the detector module in the imaging apparatus, and wherein the performance characteristics include at least one of afterglow, crosstalk, linearity, offset, and pixel operative status.

15. The detector module of claim 10 wherein the signal correction circuitry includes digital circuitry.

16. The apparatus of claim 15 wherein the signal correction circuitry and the memory are disposed in single ASIC.

17. The detector module of claim 10 wherein the detector pixels include back contact photodiodes.

* * * * *